United States Patent [19]

Rappas et al.

[11] 4,095,975

[45] Jun. 20, 1978

[54] CONTINUOUS RECOVERY OF COPPER METAL FROM ACIDIC SOLUTIONS

[75] Inventors: Alkis S. Rappas, Arlington; John N. Gerlach, Burlington, both of Mass.

[73] Assignee: Kennecott Copper Corporation, New York, N.Y.

[21] Appl. No.: 790,275

[22] Filed: Apr. 25, 1977

[51] Int. Cl.$^2$ ............................................. C22B 15/12
[52] U.S. Cl. ..................................... 75/108; 75/0.5 A; 75/117; 252/188
[58] Field of Search .................. 252/188; 260/438.1, 260/619 F; 75/0.5 A, 108, 117, 101 BE

[56] References Cited

U.S. PATENT DOCUMENTS

| | | | |
|---|---|---|---|
| 2,720,532 | 10/1955 | Umhoefer | 260/619 F |
| 3,820,979 | /0000 | Manassen | 75/117 |
| 4,032,331 | 6/1977 | Gerlach | 75/117 |
| 4,032,332 | 6/1977 | Gerlach | 75/117 |
| 4,033,765 | 7/1977 | Gerlach | 75/117 |
| 4,038,070 | 7/1977 | Rappas et al. | 75/117 |

Primary Examiner—O. R. Vertiz
Assistant Examiner—Brian E. Hearn
Attorney, Agent, or Firm—John L. Sniado; Anthony M. Lorusso

[57] ABSTRACT

A process for winning copper from acidic aqueous solutions which employs hydrogen to drive the reaction. The copper bearing liquor is treated with an organic phase comprising a quinolic reductant and a nitrile solubilized in a water immiscible solvent. Components of the two phases react to produce a nitrile ligand stabilized cuprous solution and an organic solution containing oxidized quinolic compound. After separation, the organic phase containing the spent quinolic is regenerated by hydrogenation. The cuprous ion solution is flash distilled to drive off the nitrile and to produce equimolar quantities of copper metal and cupric ions by disproportionation. The nitrile may be reabsorbed into the organic phase for reuse.

30 Claims, 1 Drawing Figure

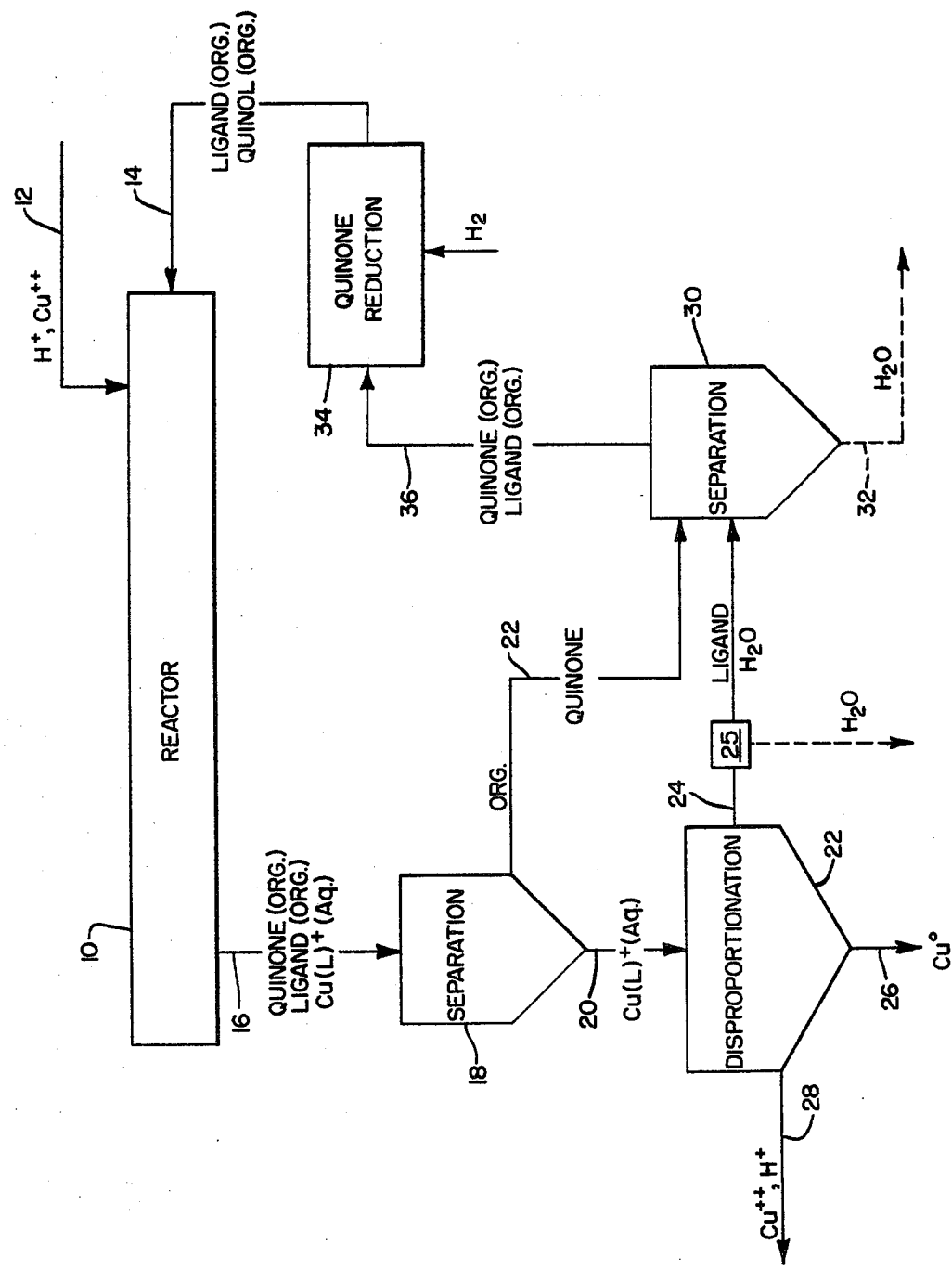

CONTINUOUS RECOVERY OF COPPER METAL FROM ACIDIC SOLUTIONS

BACKGROUND OF THE INVENTION

This invention relates to the selective recovery of copper from various acidic solutions thereof. More specifically, it relates to a continuous process for recovering a pure copper metal product from acidic leaching liquors containing cupric ions admixed with other metal ions and to reagents useful in such a process.

It is known that copper metal can be precipitated from solutions containing complexed cuprous ions by disproportionation of the complex according to the following reactions:

$$2CuL_2^+{}_{(aq)} \rightleftarrows 2Cu^+{}_{(aq)} + 4L$$

$$2Cu^+{}_{(aq)} \rightleftarrows Cu^\circ + Cu^{++}{}_{(aq)}$$

wherein L is a cuprous ion stabilizing ligand, e.g., acetonitrile. U.S. Pat. No. 3,865,744 to A. J. Parker et al. broadly describes various methods of producing and disproportionating cuprous nitrile complexes in acidic solutions. Among the disclosed methods of reducing cupric ions to cuprous nitrile complexes are: reduction with $SO_2$ gas to Chevreul's salts and dissolution of the latter in the presence of nitrile to give the cuprous nitrile complex; dissolution of crude copper metal with cupric solutions containing nitrile; and reduction of cupric to cuprous nitrile complexes by various metallic reducing agents, e.g., Ag, Fe, Ni, Zn, Cd, Co, Sn, etc.

Another technique utilizing the disproportionation phenomena is disclosed in U.S. Pat. No. 4,038,070 to Rappas et al. entitled *Low Temperature and Pressure Continuous Reduction of Copper in Acidic Solutions*. In that application, acidic sources of cupric ions are reduced by hydrogen gas in the presence of a hydrogenation catalyst and a nitrile ligand. The presence of the ligand prohibits precipitation of copper metal onto the catalyst by tying up the cuorous ions produced in the stable cuprous nitrile complex. In another embodiment of the invention disclosed in the Rappas et al. patent, acidic solutions of cupric ions are reduced to ligand stabilizing cuprous ions in an electrochemical cell. The cuprous ions produced by both embodiments of the invention of the foregoing application are ideally suited for disproportionation and lead to a copper product of high purity.

The disproportionation technique has many advantages, and the latter method of producing ligand stabilized cupric ion have many features which make the overall process economically attractive. However, there are several areas in the procedure where further improvement is possible. Specifically, under certain conditions, mixing acidic nitrile containing solutions with solutions of cupric ions of rather high concentration can lead to a "salting out" of copper salt, thus producing deposits which can hamper the smooth operation of the process. Furthermore, while catalyst poisoning by precipitation of copper metal on the catalyst is overcome in the Rappas et al. procedure, there is still the possibility that a variety of impurities commonly associated with acidic copper bearing liquors can seriously interfere with the catalytic activity of the finely divided palladium or platinum typically employed. Also, in a commercially successful embodiment, the foregoing procedures would require the use of several catalytic hydrogenation units or several electrochemical cells.

U.S. Pat. No. 3,820,979 to J. Manassen entitled *Process for the Production of Metals*, discloses a process for obtaining copper, silver, and mercury from aqueous solutions containing these values. In the process of that patent, a quinolic compound dissolved in a water immiscible organic solvent contacts an aqueous solution containing metal values of interest such as copper ions in either the cupric or cuprous state. Such contact results in oxidation of the quinolic compound to a quinonic compound in the simultaneous reduction of copper to copper metal.

In U.S. Pat. No. 4,033,765 to J. Gerlach, entitled *Improvements In the Extraction of Copper From Solutions By Reduction With Anthraquinols*, certain improvements in this organic copper reduction process are disclosed. One of the discoveries upon which the claimed invention in the Gerlach patent is based is that when a solution of $Cu^{++}$ is contacted with a known quinolic reductant, a single electron reduction of $Cu^{++}$ to $Cu^+$ proceeds very rapidly, is essentially quantitative, and unlike the two electron reduction, does not require an excess of extractant. The process disclosed in the Gerlach patent takes advantage of this discovery and provides a considerably improved quinolic organic reduction procedure characterized by reduced reductant losses and increased reaction rates. However, the procedures utilizing the quinolic reductant as disclosed in the Manassen patent and in the Gerlach patent require a series of rather expensive stirred tank reactors as well as at least one relatively difficult three phase separation.

SUMMARY OF THE INVENTION

The instant invention provides a novel copper recovery process which utilizes both disproportionation and organic reductant technologies, preserving many of the advantages of each while eliminating many of their disadvantages. In its most basic aspects, the invention is based on the following discoveries.

(1) Nitriles capable of stabilizing cuprous ions in aqueous solutions may be incorporated into the same organic solvent carrier employed in quinolic reductant systems together with the quinolic compound. Exposure of acidic copper bearing liquors to such an organic, water immiscible solution results in in-situ reduction of cupric ions to cuprous ions and simultaneous transfer of the nitrile ligands to the aqueous phase to produce ligand stabilized cuprous ions.

(2) In the foregoing procedure, a large number of organic reductants may be employed which are not operative or are marginally operative in the Manassen process.

(3) The two phase reaction can take place in a static mixer as opposed to the stirred tank reactors required in the prior art processes.

(4) The controlled introduction of the cuprous ion stabilizing ligand into the aqueous phase obviates the "salting out" problem of the prior art acetonitrile-disproportionation processes.

Thus, in one aspect, the invention provides a class of novel reagents for producing cuprous solutions suitable for further reduction.

The foregoing discoveries enable a continuous procedure to be designed which produces a copper product having the characteristic high purity of copper produced by disproportionation from acidic cupric solutions which is energy efficient and utilizes hydrogen as essentially its only consumed reagent. In the process of the invention, an aqueous acidic copper bearing liquor which may be of high concentration is contacted with a substantially water immiscible orgainc solvent containing a solubilized quinolic compound capable of reducing cupric ions to cuprous ions and a solubilized nitrile capable of stabilizing cuprous ions in aqueous solutions. The aqueous and organic phases are allowed to react to produce stablilized cuprous nitrile complex in the aqueous phase and quinonic compound in the organic phase. If the phases are separated and the stabilizing ligands are removed from the aqueous phase, e.g., by flash distillation, cuprous ions disproportionate to produce copper metal and solubilized cupric ions.

In preferred embodiments of the process, after reaction between the components and separation of the phases, the nitrile is flash distilled from the aqueous phase and resolubilized in the organic phase. The organic phase containing quinonic compound is regenerated by in-situ reduction to form quinolic compound, preferably by hydrogen in the presence of a conventional hydrogenation catalyst such as platinum or palladium. This enables the organic phase to be recirculated. Alternatively, the quinolic compound may be regenerated by hydrogen sulfide in the presence of an amine catalyst. While the nitrile ligand removed from the aqueous phase may be reintroduced either before or after the regeneration step, it is preferred that it be added prior to regeneration.

Typically, the gaseous nitrile produced will contain some water vapor. This is preferably eliminated by absorbing the gaseous nitrile directly into the organic phase, whereby the water will be separated. Alternatively, the water-nitrile mixture may be fractionally distilled to remove the water and to assist in maintaining water mass balance. The preferred nitrile ligand is acetonitrile ($CH_3CN$). The organic reductant can be a quinolic compound such as 2-(lower alkyl)-anthraquinol, e.g., 2-methyl, 2-ethyl, 2-propyl, 2-tert-butyl, 2-isopropyl, or 2-amyl anthraquinol as disclosed by Manassen. It has also been discovered that lower alkyl substituted 1-4 naphthoquinols, although their reduction potentials are generally insufficiently high for reduction to copper metal in aqueous solution, are well suited for the single electron reduction to ligand stabilized cuprous ions. The water immiscible solvent is preferably a mixed organic solvent comprising mutually miscible nonpolar and polar solvents.

In the process of the invention, equimolar quantities of metal and $Cu^{++}$ ions are produced. The solubilized cupric ions may be reduced to copper by any convenient method, but preferably they are circulated through additional stages identical to the system in which they were produced.

Accordingly, it is an object of the invention to provide a copper recovery process which is characterized by increased reaction rates and wherein the necessity of using three-phase separations and of employing stirred tank reactors is eliminated.

Another object of the invention is to provide a process for producing pure copper from highly acidic copper bearing liquors and particularly liquors containing a high $Cu^{++}$ ion concentration.

Another object of the invention is to eliminate salting out of cupric sulfate which sometimes occurs when nitrile ligands are exposed to concentrated solutions of cupric sulfate.

Still another object of the invention is to design a continuous copper recovery process utilizing an easily regenerated organic reductant wherein the aqueous phase containing the copper and impurities need not contact any catalyst used.

Another object is to provide a novel class of organic reductants which can drive the $Cu^{++}$ to $Cu^+$ reduction.

Still another object of the invention is to provide a copper metal winning procedure which produces copper powder of high purity, allows control of particle size, and allows an improved degree of flexibility of impurity control.

Yet another object of the invention is to provide a process suitable for continuous operation which enables easy control over process parameters.

These and other objects of the invention will be apparent to those skilled in the art from the following description of a preferred embodiment and from the drawing wherein the sole FIGURE is a schematic diagram illustrating one important embodiment of the overall process of the invention as it is used in the recovery of metallic copper from acidic copper bearing solutions.

DESCRIPTION OF THE PREFERRED EMBODIMENT

At the outset the invention is described in its broadest overall aspects with a more detailed description following.

The instant invention is based on the discovery that it is possible to treat acidic copper bearing liquors with a homogeneous organic solution to produce ligand stabilized cuprous ions suitable for disproportionation. The organic solution, hereinafter referred to as the organic phase, is made up principally of three components: a water immiscible carrier, a "quinolic compound" capable of reducing cupric ions to cuprous ions, and a ligand capable of stabilizing cuprous ions in aqueous solution.

The water immiscible carrier comprises an organic solvent or solvent mixture and is not directly involved in the chemistry of the overall process. Accordingly, the particular organic solvent selected for use does not form a part of the instant invention. However, it will readily be appreciated that the solvent or solvent system should be inert to all reactions taking place in the process and should be capable of dissolving the compound used as a reducing agent, the oxidized reductant produced as a by-product of the reduction, and the nitrile ligands used to stabilize the cuprous ions in aqueous solutions. These properties are best achieved by a mixed solvent system.

Suitable solvent systems are disclosed in the aforementioned Manassen patent and Gerlach patent. The preferred carriers consist of mutually miscible combinations of nonpolar solvents, such as various substituted benzenes and naphthalenes, and polar solvents. When such a solvent system is employed, the quinol is dissolved primarily in the polar solvent and the quinone in the nonpolar solvent. As suggested by the disclosure of the Gerlach patent, improved results are possible when the amount of nonpolar solvent in the mixed solvent system is greater than the amount of polar solvent. Nonlimiting examples of useful nonpolar organic solvents include xylene, toluene, naphthalenes, and various other lower alkyl substituted benzenes. Nonlimiting examples of organic polar solvents include alcohols, ketones, and esters.

The second component in the organic phase is a "quinolic compound" capable of reducing cupric ions to cuprous ions. The term "quinolic compound" as used herein refers not only to the known anthraquinol copper reductants, but also to 1-4 naphthoquinols. Such reducing agents are oxidized to anthraquinones or naphthoquinones during the single electron copper reduction. Suitable anthraquinols include 2 methyl anthraquinol, 2 ethyl anthraquinol, 2 propyl anthraquinol, 2 isopropyl anthraquinol, 2 tert-butyl anthraquinol, and 2 amyl anthraquinol. Tetrahydro anthraquinols and 2 substituted tetrahydro anthraquinols can also be used. The oxidized form of these compounds can be easily produced by condensation of a suitably substituted diene and naphthaquinone, according to the procedure of Alan et al., *Organic Synthesis*, 22, 37, (1974). The quinol can thereafter be made by hydrogenation. Suitable naphthoquinols include lower alkyl substituted 1-4 naphthoquinols such as methyl, ethyl, propyl, isopropyl, butyl, tert-butyl, amyl and pentyl 1-4 naphthaquinols. One or more of the hydrogens in the naphthaquinol may be replaced by a lower alkyl group, and the substitutent is not restricted to the "2" position.

The foregoing quinolic compounds can reduce copper in accordance with the following examplary reaction:

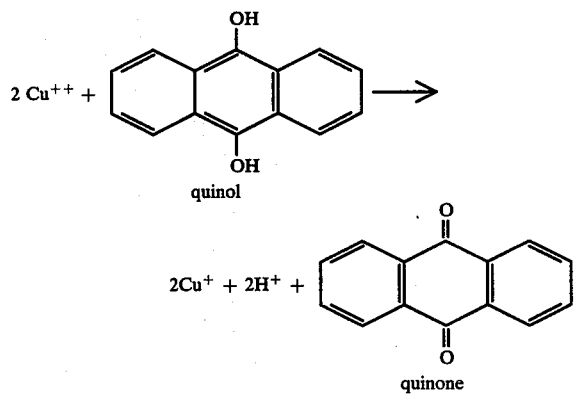

As long as the copper bearing liquor being treated contains a cuprous ion stabilized ligand and the quinol is present in less than equimolar quantities with the $Cu^{++}$, no copper metal will precipitate from the solution.

After the copper reduction, the quinone may be regenerated in accordance with the following examplary reaction:

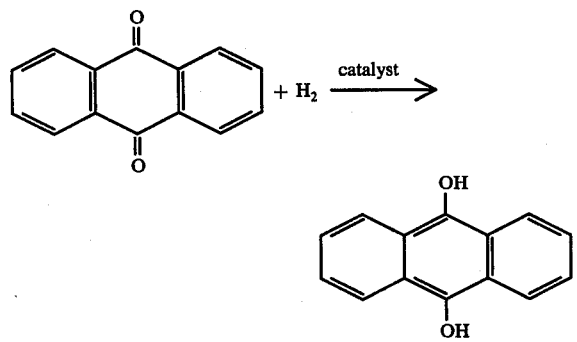

Semiquinones, such as compounds having the structural formula:

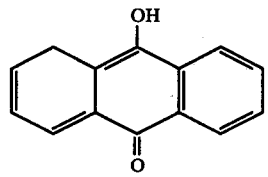

are believed to also take part in the reactions. Furthermore, it is likely that small amounts of tetrahydroquinols may be produced along with the quinol during regeneration. These too will take part in the reactions set forth above.

The third component of the organic phase is a ligand capable of stabilizing cuprous ions in acidic aqueous solutions. Nitriles are the presently preferred ligands, but other types of ligands are possible. The particular nitrile ligand selected must of course be soluble in the organic phase. The preferred ligand is acetonitrile, $CH_3CN$. However, it will be obvious to those skilled in the art that other nitriles, e.g., alkyl nitriles of the general formula RCN wherein R is a lower alkyl group may be substituted for the acetonitrile. Nonlimiting examples of such equivalent nitriles include acrylonitrile and 2-hydroxy cyanoethane.

In accordance with the invention, an organic phase as described above is contacted with an acidic aqueous solution containing cupric ions from, for example, a conventional leaching operation. The anion associated with the copper in the cupric solution has no particular significance and may be $SO_4^=$, $Cl^-$, $NO_3^-$, $C_2H_3O_2^-$, mixtures thereof, etc. As will e explained more fully below, in the process of the invention, it is not required that the aqueous phase ever contact the hydrogenation catalyst. Accordingly, there is no risk of catalyst poisoning by impurities in the copper bearing liquor.

The aqueous phase containing $Cu^{++}$ and $H^+$ ions is contacted with the organic phase. During the reaction, cupric ions are reduced to cuprous ions, essentially on a quantitive basis, and an aqueous acidic, nitrile stabilized cuprous solution results. The following reaction occurs:

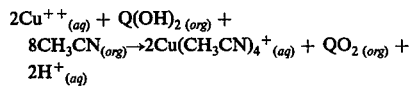

wherein $Q(OH)_2$ and $QO_2$ are the naphtho or anthra quinolic and quinonic compounds, respectively. The contact between the organic and aqueous phases needed to promote reaction can be achieved by passing the two phases through a static mixer. This amounts to a significant advantage since capital costs are lowered. The use of static mixers, as opposed to stirred tank reactors, is possible because of the favorable kinetics of the reduction set forth above. It should also be noted that the stabilizing ligand, exemplified above as $CH_3CN$, is not quantitatively transferred during the reaction and significant quantities may remain in the organic phase after reaction.

The $Cu(CH_3CN)_4^+$ which is solubilized in the aqueous solution may be disproportionated to produce pure copper metal and cupric ions in accordance with the reactions:

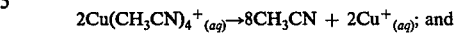

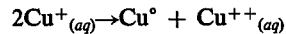

On removal of the stabilizing ligands, here again exemplified as acetonitrile, cuprous ions are left in solution. These spontaneously undergo disproportionation wherein an electron is transferred from one cuprous ion to another resulting in copper metal and a cupric ion in accordance with the above equation.

The foregoing chemistry is utilized as an integral part of an overall copper recovery system capable of winning pure copper metal from acidic cupric ion containing solutions using only hyrogen gas to drive the reduction. An example of such a process is set forth in detail below.

Referring to the drawing, stream 12 feeds an aqueous pregnant liquor containing hydrogen ions and cupric ions to a static mixer or reactor 10. Stream 14 introduces an organic phase comprising, e.g., acetonitrile, and a (lower alkyl)-naphthoquinol solubilized in an organic solvent system into reactor 10 together with the aqueous phase. The two phases contact in the reactor to produce $Cu(CH_3CN)_4^+$ in the aqueous phase. The (lower alkyl)-naphthoquinol is oxidized to (lower alkyl)-naphthoquinone, a pair of hydrogen ions being given up which are absorbed into the aqueous phase. The naphthoquinone remains dissolved primarily in the organic phase. In addition, some of the acetonitrile ligand remains in the organic phase.

During this reaction, hydrogen ions from the quinol and acetonitrile ligands are transferred from the organic phase to the aqueous phase. This relatively controlled introduction of acetonitrile into the cupric solution, in conjunction with the fast reduction rate, eliminates salting out of cupric salts which sometimes occurs in prior art processes when the cupric solution is of high concentration.

Both phases exit reactor 10 via stream 16 and are partitioned in separation tank 18. The aqueous phase, which is now more acidic than the solution introduced through stream 12 because of the introduction of additional hydrogen ions received from the quinolic extractant, is passed via stream 20 to disproportionation apparatus 22, the organic phase containing the oxidized quinol (quinone) exits separation tank 18 via stream 20.

In disproportionation tank 22, the acetonitrile is removed, e.g., by flash distillation using live steam. Acetonitrile containing some water vapor exits tank 22 in the vapor phase via stream 24. The destabilized cuprous ions, under these conditions, spontaneously disproportionate to produce copper metal which is collected via solid stream 26 and an acidic cupric ion containing solution which exits via stream 28.

The ratio of copper metal to copper ions in the acidic solution is determined mainly by the simultaneous equilibria:

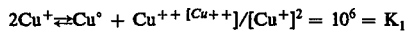

$Cu^+ + 2CH_3CN \rightleftharpoons Cu(CH_3CN)_2^+$

$\log K_2 = 4.35$

Depending on the $Cu^{30}/CH_3CN$ and the $CH_3CN/H_2O$ ratios, a third and fourth molecule of acetonitrile may coordinate with the cuprous ions.

As indicated above, copper precipitates as a powder which is then separated from solution, and, if desired, treated by conventional technology by dewatering, drying, briquetting, melting, and casting in order to obtain a more marketable product. Conventional seeding technology can improve particle size.

For every mole of copper metal produced during disproportionation, one mole of cupric ions is also produced, and obviously, this oxidized copper must be recovered in order for the process to have any commercial significance.

One method of recovering the copper is to simply reintroduce the aqueous acidic copper bearing liquor into the process stream such as at line 12. While this procedure will work, it ultimately requires a purge since the H+ and anion concentration reapidly build up, and water mass balance is adversely affected.

There are several other theoretically feasible methods of recovery available. For instance, copper could be recovered by electrowinning. If this method were used, the copper produced would be copper powder and electrowon copper at an approximate ratio of one to one. Another alternative would be cementation on scrap iron.

U.S. Pat. No. 4,038,070 to Rappas et al. discloses another method which could be applied to treat the liquor in stream 28. The Rappas procedure involves an intermediate step of precipitating copper on a hydrogenation catalyst in the presence of hydrogen.

However, the preferred method of treating the acidic pregnant liquor of stream 28 is by utilizing it as the feed liquor in another system (not shown) such as the one disclosed herein. Such a procedure results in another, still more acidic pregnant liquor. This however could be treated in still another stage. After a suitable number of stages, the copper bearing pregnant liquor from the last disproportionation could be recycled to the leaching and used to pick up more copper values.

The overhead vapors from the flash distillation taking place in disproportionation tank 22 will contain acetonitrile and some water. It is possible to remove the water by fractionation, such as in fractionator 25, and if the pregnant liquor of stream 28 is recirculated to stream 12, this technique would aid in maintaining water mass balance. If staging is used, it is preferred to simply absorb the acetonitrile-water vapor gaseous mixture passing through stream 24 directly into the organic phase in separation tank 30. In this case, a small volume of water containing some acetonitrile is separated in tank 30 via stream 32.

The organic phase, now reloaded with acetonitrile essentially to its initial level, is then introduced into a catalytic hydrogenation reactor 34 via stream 36. The hydrogenation reactor 34 is of a type generally well known in the art and comprises a palladium or platinum catalyst, preferably immobilized on a suitable support, which will enable the quinonic compound to be reduced to quinolic compound, in situ.

After hydrogenation as described above, the organic phase, now including the regenerated quinol and acetonitrile, is reintroduced via stream 14 into reactor 10 where it is utilized to reduce more copper.

Alternatively, it is possible to introduce the nitrile produced by flash distillation in disproportionation tank 22 into the organic phase after the quinonic compound has been regenerated by hydrogenation. In this case, the nitrile would be introduced at a suitable point beyond the hydrogenator 34, e.g., at some point in stream 14.

The foregoing process can treat highly acidic and concentrated pregnant liquors which for economic reasons are poorly suited for use in either the quinolic reductant or the catalytic or electrolytic single electron reduction procedures described in the prior art discussed above. Furthermore, because of the high reaction rate associated with the one electron reduction by quinolic compounds, a static mixer may be used. Since the reduction is carried only to the cuprous state, there is a wider selection of quinone-quinol couples and hydrogenation catalysts available. The presence of the acetonitrile in the organic phase makes it possible to treat pregnant liquors of a much higher copper concentration and higher acidity than in the conventional quinolic reduction procedure of Manassen or the improved procedure set forth in the aforementioned Patent to J. A. Gerlach.

The invention will be further understood from the following nonlimiting examples.

EXAMPLE 1

Six grams of 2-t-butyl anthraquinone were dissolved in a mixed solvent system comprising 60 ml. xylene and 40 ml. decanol at 50°–55° C. under an inert atmosphere. An aqueous alkaline solution of sodium dithionite (140 ml., 0.5 M $Na_2S_2O_4$, 2.0 M NaOH) was then thoroughly mixed with the above organic under an inert atmosphere at 50° C. for 45 minutes to reduce the quinone to quinol. The aqueous phase was then acidified with phosphoric acid so that the organic phase was loaded with quinol. After separation of the phases, the organic was washed twice with 40 ml. of 0.5 M $Na_2CO_3$. Fifteen ml. of acetonitrile were then added to 50 ml. of the washed organic, and the acetonitrile-quinol-organic mix was added to a stirred reactor equipped with a refluxing condenser.

Fifty ml. of a 31.25 g/l $Cu^{++}$ solution (pH = 1.0) was then added to the reactor and stirring was commenced at 50° C. (time = 0). One-half milliliter samples were then taken from the aqueous phase at two-minute intervals and were analyzed for cuprous and total copper content. At the conclusion of the reduction, the phases were separated and the volume of the aqueous phase was found to be 61 ml., the increase in volume being due to the phase shift of acetonitrile. As can be seen from Table I set forth below, the single electron reduction was very fast.

Table I

| Time (min.) | Reduction $[Cu^+]/[Cu_T]$ (%) | $[Cu^+]$ g/l | $[Cu_T]$ g/l |
| --- | --- | --- | --- |
| 0 | 0.0 | 0 | 25.61 |
| 2 | 67.4 | 16.78 | 24.90 |
| 4 | 74.0 | 18.87 | 25.50 |
| 6 | 74.7 | 18.45 | 24.70 |

EXAMPLE 2

The procedure in Example 1 was repeated except that 2 methyl-1,4,napthoquinol was used in place of the anthraquinol of Example 1. The composition of the phases and results are set forth below.

Table II

| Organic | |
| --- | --- |
| 2.0 g | 2-methyl-1,4-naphthoquinone |
| 30 ml. | xylene |
| 20 ml. | decanol |
| 20 ml. | acetonitrile |
| Aqueous (50 ml. total) | |
| 31.25 g/l $Cu^{++}$ | |

Table II-continued 0.0 g/l $Cu^+$
pH = 1.0
Temp. = 50° C
66 ml. of aqueous phase (including acetonitrile) were present after reduction.

| Time (min.) | Reduction $[Cu^+]/[Cu_T]$(%) | $[Cu^+]$g/l | $[Cu_T]$g/l |
| --- | --- | --- | --- |
| 0 | 0.0 | 0 | 23.67 |
| 0.5 | 79.5 | 18.87 | 23.75 |
| 2.0 | 81.0 | 18.87 | 23.30 |

EXAMPLE 3

A solution of 5.6 g. of 2-methyl-1,4-napthoquinone in 60 ml. xylene, 40 ml. decanol, and 40 ml. acetonitrile is added to a stirred reactor equipped with a refluxing condenser at 50° C. Under approximately one atmosphere of hydrogen, approximately 1 gram of a conventional hydrogenation catalyst (5% palladium on aluminum powder) is added. The hydrogenation is complete within one half hour, and 2-methyl-1,4-napthoquinol is separated from the solid catalyst under a non-oxidizing atmosphere.

Seventy ml. of the quinol containing organic is then mixed with 50 ml. of an aqueous cupric solution. Compositions and results are set forth below.

Table III

| Organic | |
| --- | --- |
| 2-methyl-1,4-naphthoquinone | 2.8 g |
| xylene | 30 ml. |
| decanol | 29 ml. |
| acetonitrile | 20 ml. |
| Aqueous (50 ml. total volume) | |
| $Cu^{++}$ | 31.25 |
| $Cu^+$ | 0.0 |
| pH | 1.0 |

Volume of aqueous phase after reduction is 68.5 ml.

| Time (min.) | Reduction $[Cu^+]/[Cu_T]$(%) | $[Cu^+]$g/l | $[Cu_T]$g/l |
| --- | --- | --- | --- |
| 0 | 0.0 | 0 | 22.81 |
| 1.0 | 98.8 | 22.22 | 22.50 |

In all of the above examples, the discrepancy between the $Cu^{++}$ concentration of the aqueous phase and the total copper content at time zero is due to the phase shift of nitrile which takes place on mixing of the phases prior to any reaction.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of this claims are therefore intended to be embraced therein.

We claim:

1. A process for recovering copper from an aqueous phase comprising an acidic copper bearing liquor, said process comprising the steps of:
    A. contacting the aqueous phase with an organic phase comprising substantially water immiscible organic solvent which contains:
        1. a solubilized quinolic compound capable of reducing cupric ions to cuprous ions; and
        2. a solubilized nitrile capable of stabilizing cuprous ions in aqueous solution;

B. allowing components of the organic phase to react with copper values to produce stabilized cuprous nitrile complex in the aqueous phase and a quinonic compound in the organic phase;

C. separating the aqueous and organic phases; and

D. removing the nitrile from the complex in the aqueous phase to disproportionate the cuprous ions to produce copper metal and water solubilized cupric ions.

2. The process as set forth in claim 1 wherein the separated organic phase is recycled to step A.

3. The process as set forth in claim 1 comprising the further steps of:

E. solubilizing the nitrile removed in step D in the separated organic phase; and F. recycling the resulting organic solution to step A.

4. The process as set forth in claim 1 wherein step D is effected by distillation of the cuprous nitrile complex.

5. The process as set forth in claim 4 wherein the distillation is a flash distillation, gaseous nitrile is produced, and said gaseous nitrile is transported to the organic phase and solubilized therein.

6. The process as set forth in claim 5 wherein the gaseous nitrile contains water vapor and the vapor is removed by fractional distillation prior to solubilizing the nitrile in the organic phase.

7. The process as set forth in claim 1 comprising the further step of reducing the solubilized cupric ions produced in step D to copper metal.

8. The process as set forth in claim 7 wherein the reduction is effected by an additional stage wherein the aqueous cupric ions are contacted with an organic phase comprising a substantially water immiscible organic solvent, a solubilized quinolic compound capable of reducing cupric ions to cuprous ions, and a solubilized nitrile capable of stabilizing cuprous ions to produce ligand stabilized cuprous ions in the aqueous phase.

9. The process as set forth in claim 1 comprising the further steps of:

regenerating the quinonic compound produced in step B by reducing the quinonic compound to quinolic compound; and recycling the regenerated compound to step A.

10. The process as set forth in claim 9 wherein the quinonic compound is reduced in situ with hydrogen in the presence of a hydrogenation catalyst.

11. The process as set forth in claim 10 wherein acetonitrile is present together with the quinonic compound.

12. The process as set forth in claim 9 wherein the quinonic compound is reduced in situ with $H_2S$ in the presence of an amine catalyst.

13. The process as set forth in claim 1 wherein the nitrile is $CH_3CN$.

14. The process as set forth in claim 1 wherein the quinolic compound is a 2-(lower alkyl)-anthraquinol selected from the group consisting of 2 methyl, 2 ethyl, 2 propyl, 2-tert-butyl, 2-isopropyl, and 2 amyl anthraquinol.

15. The process as set forth in claim 1 wherein the quinolic compound is a 1-4 napthoquinol substituted with a lower alkyl group selected from the group consisting of methyl, ethyl, propyl, isopropyl, butyl, isobutyl, pentyl, and combinations thereof.

16. The process as set forth in claim 1 wherein the water immiscible organic solvent is a mixed solvent comprising a nonpolar solvent and a polar solvent.

17. A process for recovering copper from an aqueous phase comprising an acidic copper bearing liquor, said process comprising the steps of:

A. contacting the aqueous phase with an organic phase comprising a substantially water immiscible organic solvent containing:

(1) a solubilized quinolic compound capable of reducing cupric ions to cuprous ions; and (2) a solubilized nitrile capable of stabilizing cuprous ions in aqueous solutions;

B. allowing components of the organic phase to react with copper values to produce a stabilized cuprous nitrile complex in the aqueous phase and quinonic compound in the organic phase;

C. separating the aqueous and organic phases;

D. removing the nitrile from the complex in the aqueous phase to produce nitrile vapor and to disproportionate the cuprous ions to copper metal and solubilized cupric ions;

E. reducing the quinonic compound produced in the organic phase in step B to quinolic compound;

F. siolubilizing the nitrile vapor produced in step D in the organic phase; and

G. recycling the organic phase containing the nitrile and quinolic compound to step A.

18. The process as set forth in claim 17 wherein step F is effected prior to step E.

19. The process as set forth in claim 17 wherein the nitrile is $CH_3CN$.

20. The process as set forth in claim 17 wherein the quinolic compound is a 2-(lower alkyl) anthraquinol selected from the group consisting of 2 methyl, 2 ethyl, 2 propyl, 2-tert-butyl, 2-isopropyl, and 2 amyl anthraquinol.

21. The process as set forth in claim 17 wherein the quinolic compound is a 1-4 napthoquinol substituted with a lower alkyl group selected from the group consisting of methyl, ethyl, propyl, isopropyl, butyl, isobutyl, pentyl, and combinations therof.

22. The process as set forth in claim 17 wherein step D is effected by flash distillation.

23. The process as set forth in claim 17 wherein step E is effected by reacting the quinonic compound, in situ, with hydrogen in the presence of a hydrogenation catalyst.

24. The process as set forth in claim 17 wherein step E is effected by reacting the quinonic compound, in situ, with $H_2S$ in the presence of an amine catalyst.

25. The process as set forth in claim 17 wherein the water immiscible solvent is a mixed solvent comprising a nonpolar solvent and a polar solvent.

26. The process as set forth in claim 17 comprising the further step of reducing the $Cu^{++}$ produced in step D to copper metal.

27. The process as set forth in claim 26 wherein the reducing step is effected by recycling the solubilized cupric ions to step A and repeating said process.

28. The process as set forth in claim 26 wherein said reducing step includes the step of disproportionating a ligand stabilized cuprous solution produced from the $Cu^{++}$ produced in step D.

29. The process as set forth in claim 26 wherein said reducing step includes the step of precipitating copper metal on a hydrogenation catalyst.

30. A process for producing an aqueous solution of ligand stabilized cuprous ions suitable for further reduction to copper metal from an aqueous phase comprising an acidic solution containing cupric ions, said process comprising the steps of:

providing an organic phase comprising a substantially water immiscible organic solvent containing a solubilized quinolic compound capable of reducing cupric ions to cuprous ions and nitrile ligands capable of stabilizing cuprous ions in aqueous solutions;

contacting the organic and aqueous phases in a reaction zone to allow the quinolic compound to reduce cupric ions to cuprous ions and to effect transfer of said ligands from the organic to the aqueous phase; and separating a ligand stabilized cuprous solution from the reaction zone.

* * * * *